US00PP23682P2

(12) United States Plant Patent
Dümmen

(10) Patent No.: US PP23,682 P2
(45) Date of Patent: Jun. 18, 2013

(54) ***BIDENS* PLANT NAMED 'DUEBIGONBI'**

(50) Latin Name: *Bidens ferulifolia*
Varietal Denomination: Duebigonbi

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 22 days.

(21) Appl. No.: 13/317,905

(22) Filed: Oct. 31, 2011

(51) Int. Cl.
*A01H 5/00* (2006.01)

(52) U.S. Cl.
USPC ..... Plt./410

(58) Field of Classification Search
USPC ..... Plt./410
See application file for complete search history.

*Primary Examiner* — Susan McCormick Ewoldt
(74) *Attorney, Agent, or Firm* — C. A. Whealy

(57) ABSTRACT

A new and distinct cultivar of *Bidens* plant named 'Duebigonbi', characterized by its relatively compact and mounding plant habit; moderately vigorous growth habit; freely branching habit; freely flowering habit; large inflorescences with bright yellow-colored ray florets and darker yellow-colored disc florets; and strong peduncles that hold the inflorescences above and beyond the foliar plane.

1 Drawing Sheet

Botanical designation: *Bidens ferulifolia.*
Cultivar denomination: 'DUEBIGONBI'.

BACKGROUND OF THE INVENTION

The present invention relates to a new and distinct cultivar of *Bidens* plant, botanically known as *Bidens ferulifolia* and hereinafter referred to by the name 'Duebigonbi'.

The new *Bidens* plant is a product of a planned breeding program conducted by the Inventor in Rheinberg, Germany. The objective of the breeding program is to create new compact and mounding *Bidens* plants with numerous large inflorescences.

The new *Bidens* plant originated from a cross-pollination made by the Inventor in Rheinberg, Germany in July, 2008 of a proprietary selection of *Bidens ferulifolia* identified as code number B07-1002-003, not patented, as the female, or seed, parent with a proprietary selection of *Bidens ferulifolia* identified as code number B07-1108-002, not patented, as the male, or pollen, parent. The new *Bidens* plant was discovered and selected by the Inventor as a single flowering plant from within the progeny of the stated cross-pollination in a controlled greenhouse environment in Rheinberg, Germany in May, 2010.

Asexual reproduction of the new *Bidens* plant by vegetative cuttings in a controlled environment in Rheinberg, Germany since June, 2010 has shown that the unique features of this new *Bidens* plant are stable and reproduced true to type in successive generations.

SUMMARY OF THE INVENTION

Plants of the new *Bidens* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Duebigonbi'.

These characteristics in combination distinguish 'Duebigonbi' as a new and distinct *Bidens* plant:

1. Relatively compact and mounding plant habit.
2. Moderately vigorous growth habit.
3. Freely branching habit.
4. Freely flowering habit.
5. Large inflorescences with bright yellow-colored ray florets and darker yellow-colored disc florets.
6. Strong peduncles that hold the inflorescences above and beyond the foliar plane.

Plants of the new *Bidens* differ primarily from plants of the female parent selection in the following characteristics:

1. Plants of the new *Bidens* are more compact than plants of the female parent selection.
2. Plants of the new *Bidens* have larger inflorescences than plants of the female parent selection.

Plants of the new *Bidens* differ primarily from plants of the male parent selection in the following characteristics:

1. Plants of the new *Bidens* are more compact than plants of the male parent selection.
2. Plants of the new *Bidens* have larger inflorescences than plants of the male parent selection.

Plants of the new *Bidens* can be compared to plants of *Bidens ferulifolia* 'Solaire Jumbo Gold', not patented. In side-by-side comparisons conducted in Rheinberg, Germany, plants of the new *Bidens* differed from plants of 'Solaire Jumbo Gold' in the following characteristics:

1. Plants of the new *Bidens* had longer internodes than plants of 'Solaire Jumbo Gold'.
2. Plants of the new *Bidens* had larger leaves than plants of 'Solaire Jumbo Gold'.
3. Plants of the new *Bidens* had larger inflorescences than plants of 'Solaire Jumbo Gold'.

BRIEF DESCRIPTION OF THE PHOTOGRAPH

The accompanying photograph illustrates the overall appearance of the new *Bidens* plant showing the colors as true as it is reasonably possible to obtain in colored reproductions of this type. Colors in the photograph may differ slightly from the color values cited in the detailed botanical description which accurately describe the colors of the new *Bidens* plant. The photograph comprises a side perspective view of a typical flowering plant of 'Duebigonbi' grown in a container.

DETAILED BOTANICAL DESCRIPTION

The aforementioned photograph and following observations and measurements describe plants grown in 12-cm containers during the summer in a glass-covered greenhouse in Rheinberg, Germany under conditions and practices which approximate those generally used in commercial *Bidens* production. During the production of the plants, day and night temperatures averaged 18° C. and light levels averaged 4,500 lux. Plants were pinched one time about three weeks after planting. Plants were twelve weeks old when the photograph and description were taken. In the following description, color references are made to The Royal Horticultural Society Colour Chart, 1995 Edition, except where general terms of ordinary dictionary significance are used Botanical classification: *Bidens ferulifolia* 'Duebigonbi'.

Parentage:

*Female parent*.—Proprietary selection of *Bidens ferulifolia* identified as code number B07-1002-003, not patented.

*Male parent*.—Proprietary selection of *Bidens ferulifolia* identified as code number B07-1108-002, not patented Propagation:

*Type*.—By vegetative cuttings.

*Time to initiate roots, summer*.—About five days at about 20° C.

*Time to initiate roots, winter*.—About seven days at about 20° C.

*Time to produce a rooted young plant, summer*.—About three weeks at about 20° C.

*Time to produce a rooted young plant, winter*.—About four weeks at about 20° C.

*Root description*.—Fine, fibrous; color, close to 155B.

*Rooting habit*.—Freely branching; moderately dense.

Plant description:

*Plant and growth habit*.—Relatively compact, upright, outwardly spreading and mounding plant habit; moderately vigorous growth habit.

*Branching habit*.—Freely branching habit with lateral branches potentially forming at every node.

*Plant height*.—About 13 cm.

*Plant diameter or spread*.—About 23 cm.

*Lateral branches*.—Length: About 13 cm. Diameter: About 3 mm. Internode length: About 2 cm. Strength: Strong. Texture: Pubescent. Color: Close to 144A.

Foliage description:

*Arrangement*.—Opposite, simple.

*Length*.—About 2.7 cm.

*Width*.—About 3.6 cm.

*Shape*.—Roughly deltoid; pinnatisect.

*Apex*.—Apiculate.

*Base*.—Acute.

*Margin*.—Deeply incised; laciniate.

*Texture, upper and lower surfaces*.—Smooth, glabrous.

*Venation pattern*.—Pinnate.

*Color*.—Developing leaves, upper surface: Close to 147A. Developing leaves, lower surface: Close to 147B. Fully expanded leaves, upper surface: Close to 147A; venation, close to 147A. Fully expanded leaves, lower surface: Close to 146A; venation, close to 147A.

*Petioles*.—Length: About 3.5 mm. Diameter: About 1 mm. Texture, upper and lower surfaces: Smooth, glabrous. Color, upper and lower surfaces: Close to 144A.

Inflorescence description:

*Appearance*.—Single (daisy) inflorescence form with ray and disc florets; inflorescences positioned above and beyond the foliar plane on strong peduncles; inflorescences face upright to outwardly.

*Flowering habit*.—Freely flowering habit; about 30 inflorescences per plant.

*Fragrance*.—None detected.

*Natural flowering season*.—Plants flower continuously during the spring in Germany; early flowering habit, plants begin flowering about five weeks after planting.

*Inflorescence longevity*.—Inflorescences last about one week on the plant; inflorescences persistent.

*Inflorescence bud*.—Height: About 6 mm. Diameter: About 4 mm. Shape: Ovoid. Color: Close to 144A.

*Inflorescence size*.—Diameter: About 4.5 cm. Depth (height): About 1.5 cm. Disc diameter: About 7 mm. Receptacle diameter: About 4 mm. Receptacle height: About 1.2 mm. Receptacle color: Close to 146A.

*Ray florets*.—Length: About 2.1 cm. Width: About 1 cm. Shape: Elliptical to ovate. Apex: Emarginate. Base: Obtuse. Margin: Entire. Texture, upper and lower surfaces: Smooth, glabrous. Number of ray florets per inflorescence: About eight arranged in a single whorl. Color: When opening, upper surface: Close to 14A. When opening, lower surface: Close to 12A. Fully opened, upper surface: Close to 14A; color becoming closer to 17A with development. Fully opened, lower surface: Close to 13A; color becoming closer to 17A with development.

*Disc florets*.—Shape: Tubular; apex dentate. Length: About 8 mm. Diameter: About 1.5 mm. Number of disc florets per inflorescence: About 50. Color, when opening: Apex: Close to 162A. Mid-section: Close to 199A. Base: Close to 155C. Color, fully opened: Apex: Close to 14A. Mid-section: Close to 199B. Base: Close to 1B.

*Phyllaries*.—Quantity per inflorescence: About eight in a single whorl. Length: About 4 mm. Width: About 1.2 mm. Shape: Elongated elliptical. Apex: Acute. Base: Truncate. Margin: Entire. Texture, upper and lower surfaces: Smooth, glabrous. Color, upper and lower surfaces: Close to 144A.

*Peduncles*.—Length, terminal peduncle: About 8.4 cm. Length, fourth peduncle: About 6.5 cm. Diameter: About 0.8 mm. Strength: Strong; flexible. Aspect: Upright to outwardly holding inflorescences above and beyond the foliar plane. Texture: Smooth, glabrous. Color: Close to 144A.

*Reproductive organs*.—Androecium: Present on disc florets only. Quantity per disc floret: One. Filament length: About 2 mm. Filament color: Close to 7A. Anther shape: Oval. Anther length: About 2.5 mm. Anther color: Close to 200C. Pollen amount: Scarce. Pollen color: Close to 7A. Gynoecium: Present on ray and disc florets. Pistil length: About 7 mm. Style length: About 4 mm. Style color: Close to 9C. Stigma shape: Bifurcate. Stigma color: Close to 15A. Ovary color: Close to 145A.

*Seeds*.—Quantity per inflorescence: About 40 to 50. Length: About 7 mm. Diameter: About 0.8 mm. Color: Close to 200A.

Disease/pest resistance: Plants of the new *Bidens* have not been shown to be resistant to pathogens and pests common to *Bidens*.

Garden performance: Plants of the new Clematis have exhibited good tolerance to rain and wind and have been observed to tolerate temperatures from about 5° C. to about 40° C.

It is claimed:

1. A new and distinct *Bidens* plant named 'Duebigonbi' as illustrated and described.

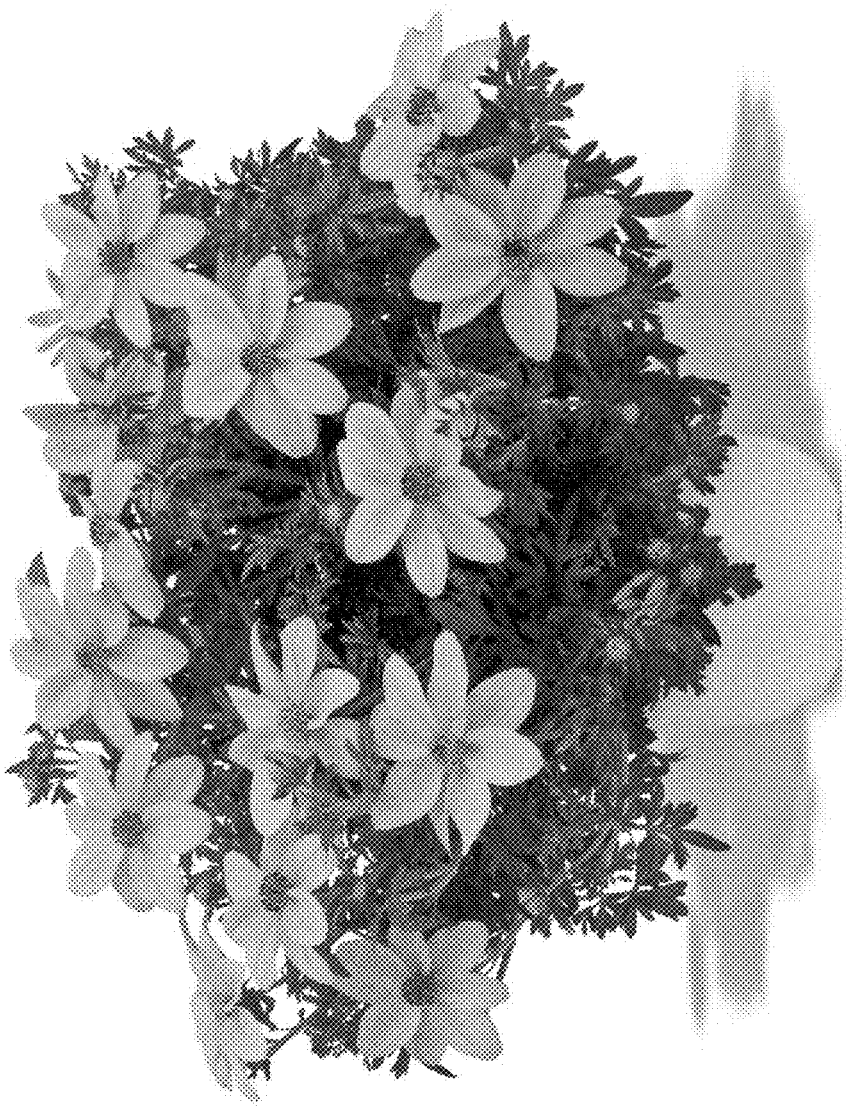

* * * * *